United States Patent [19]

Khanna et al.

[11] Patent Number: 4,847,195
[45] Date of Patent: Jul. 11, 1989

[54] GLUCOSE-6-PHOSPHATE DEHYDROGENASE CONJUGATES USEFUL IN POLYIODOTHYRONINE ASSAYS

[75] Inventors: Pyare Khanna; Kirk Schulkamp, both of San Jose, Calif.

[73] Assignee: Syntex (U.S.A.) Inc., Palo Alto, Calif.

[21] Appl. No.: 125,805

[22] Filed: Nov. 24, 1987

Related U.S. Application Data

[63] Continuation of Ser. No. 739,732, May 31, 1985, abandoned.

[51] Int. Cl.$^4$ ................ G01N 33/536; G01N 33/542
[52] U.S. Cl. ............................................ 435/7; 435/14; 435/26; 435/188; 436/500
[58] Field of Search .................. 435/7, 14, 26, 188; 436/500

[56] References Cited

U.S. PATENT DOCUMENTS

| | | | |
|---|---|---|---|
| 3,817,837 | 6/1974 | Rubenstein et al. | 435/7 |
| 3,875,011 | 4/1975 | Rubenstein et al. | 435/188 X |
| 4,039,385 | 8/1977 | Ullman | 435/18 |
| 4,040,907 | 8/1977 | Ullman | 435/12 |
| 4,043,872 | 8/1977 | Blakemore et al. | 435/188 X |
| 4,376,825 | 3/1983 | Rubenstein | 435/188 |
| 4,410,633 | 10/1983 | Herti et al. | 436/500 |

OTHER PUBLICATIONS

Malvano: "Immunoenzymatic Assay Techniques", ed. R. Malvano, Martinus Nijhoff Publisher, The Hague, 1980, pp. 59–65.
United States Patent Office: Classification Definitions, Class 260, 1971.
United States Patent Office: Classification Definitions, Class 260, p. 260-4A, Oct. 1971.

*Primary Examiner*—Robert J. Warden
*Assistant Examiner*—Robert Benson
*Attorney, Agent, or Firm*—Theodore J. Leitereg

[57] ABSTRACT

Polyiodothyronine analog conjugates to glucose-6-phosphate dehydrogenase (G6PDH) are provided which find use in the determination of polyiodothyronine compounds, particularly thyroxine, normally in physiological fluids, such as serum. The G6PDH enzyme activity can be substantially reduced when bound to antibodies specific to polyiodothyronine as compared to the free or unbound polyiodothyronine analog enzyme conjugates. The polyiodothyronine analog is conjugated to the G6PDH by a linking group having a chain one atom in length.

11 Claims, No Drawings

GLUCOSE-6-PHOSPHATE DEHYDROGENASE CONJUGATES USEFUL IN POLYIODOTHYRONINE ASSAYS

This is a continuation of pending application Ser. No. 739,732, filed May 31, 1985 now abandoned, incorporated herein by reference.

BACKGROUND OF THE INVENTION

1. Field of the Invention

Thyroxine is an important hormone in the mammalian physiology, being excreted by the thyroid gland. The measurement of thyroxine is an important diagnostic tool in the determination of disease. Various techniques have been used for the determination of thyroxine, including radioimmunoassay, competitive protein binding, chromatography, etc. These techniques suffer from a number of disadvantages in being difficult to carry out and in the case of radioimmunoassay having unstable reagents.

2. Description of the Prior Art

U.S. Pat. No. 3,817,837 describes enzyme immunoassays. U.S. Pat. No. 4,040,907 discloses iodothyronine enzyme conjugates. U.S. Pat. No. 4,171,244 discloses enzyme-bound-polyiodothyronine. A polyiodothyronine immunoassay is described in U.S. Pat. No. 4,043,872. U.S. Pat. No. 4,121,975 teaches a pretreatment of samples for polyiodothyronine assays. Enzyme immunoassays with glucose-6-phosphate dehydrogenase are described in U.S. Pat. No. 3,875,011. A method for the measurement of free thyroxine or 3,5,3'-triiodothyronine in a liquid sample is described in U.S. Pat. No. 4,410,633. Iodothyronine immunogens and antibodies are taught in U.S. Pat. No. 4,399,121. A thyroxine radioimmunoassay is described in U.S. Pat. No. 4,018,883. A radioimmunoassay for measurement of thyroxine and triiodothyronine in blood serum is disclosed in U.S. Pat. No. 3,911,096. A radioimmunoassay method for triiodothyronine and thyroxine is taught in U.S. Pat. No. 3,928,553.

SUMMARY OF THE INVENTION

Polyiodothyronine analogs (PIA) conjugated to glucose-6-phosphate dehydrogenase (G6PDH) are provided for use in immunoassays. The G6PDH conjugates are capable of competing with polyiodothyronine in a sample for antibody binding sites. The binding of the antibody to the PIA-G6PDH conjugate substantially decreases the enzymatic activity of the enzyme conjugate. By determining the enzymatic activity of an assay solution containing the sample in relation to known standards, the amount of polyiodothyronine in the sample can be determined.

The polyiodothyronine analogs are conjugated to the G6PDH by a linking group one atom in length.

DESCRIPTION OF THE SPECIFIC EMBODIMENTS

The compositions of this invention are polyiodothyronine analogs conjugated to G6PDH, where the enzymatic activity of the enzyme conjugate is substantially decreased when bound to an antibody specific for polyiodothyronine. The polyiodothyronine analogs are conjugated to G6PDH by a linking group having a chain one atom in length. The linkage will frequently involve a non-oxo-carbonyl group, including the nitrogen and sulfur analogs thereof, or a sulfonyl group. When a non-oxo-carbonyl group or sulfonyl group is the linking group, it will be bound to amino groups on the G6PDH. (Non-oxo-carbonyl intends a carbonyl group substituted with at least one heteroatom. For the purposes of this disclosure non-oxo-carbonyl shall include the carbonyl group of carboxylic acids

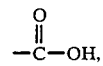

the nitrogen containing iminocarbonyl group of amidic acids

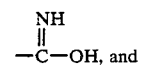

the sulfur containing thionocarbonyl group of thio acids

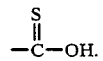

The sulfonyl group is derived from sulfonic acid

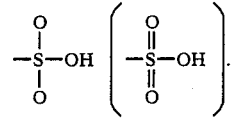

Any of the above non-oxo-carbonyl groups or the sulfonyl group may be bonded to an amine to form an amide by displacement of the hydroxyl.)

The number of PIAs conjugated to the enzyme will be at least 1, more usually at least 2, generally not exceeding 12, more usually not exceeding 10, and preferably within the range of about 3 to 8 on the average. The PIA differs from thyroxine by the absence of the alanine group and may have 1 to 4 of the iodines replaced by isosteric groups such as bromine and tert-butyl and may have one of the iodines replaced by hydrogen wherein no more than one iodine is replaced by hydrogen.

The enzyme conjugate will be capable of being employed in an immunoassay so that in combination with a receptor, preferably an antibody, and the unknown sample suspected of containing a thyronine derivative, one is able to determine the amount of the thyronine derivative in the unknown by comparison of the enzymatic activity of the assay sample compared to known standards.

For the most part, the PIA-G6PDH conjugates will have the following formula:

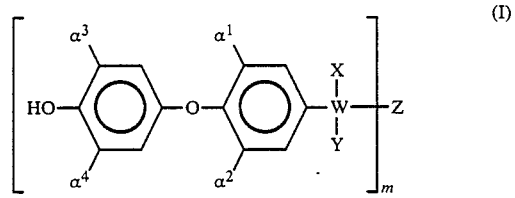

wherein:

Z is G6PDH bonded at other than its active site; by "active site" is intended those amino acid units or groups necessary for enzyme activity;

m is a number between 1 and 16, usually in the range of 2 to 12, and preferably in the range of 3 to 8;

$\alpha^{1-4}$ are usually iodine, bromine or tert-butyl, preferably iodine, although one can be hydrogen;

W is carbon or sulfur;

X is oxygen when W is sulfur; or when W is carbon, X may be taken together with Y to form a double bond to oxygen (oxo), nitrogen, sulfur or carbon wherein the carbon may contain two substituents, each substituent having 1 to 5 atoms selected from the group consisting of carbon, hydrogen, oxygen, nitrogen and sulfur, such as carboxy, lower alkyl or lower alkyl substituted with hydroxy, amino, alkoxy, carboxy, thio, etc., and the like; or X is otherwise hydrogen; and Y is oxygen when W is sulfur; or Y is a substituent having 1 to 5 atoms selected from the group consisting of carbon, hydrogen, oxygen, nitrogen, and sulfur, such as lower alkyl or carboxy, lower alkyl substituted with hydroxy, carboxy, amino, alkoxy, thio, etc., and the like. Exemplary of such compounds are 4-(4-hydroxy-3,5-diiodophenoxy)-3,5-diiodobenzoic acid or 4-(4-hydroxy-3-iodophenoxy)-3,5-diiodobenzoic acid conjugated to G6PDH by means of amide linkages.

For the most part, the G6PDH conjugates of this invention will have the following formula:

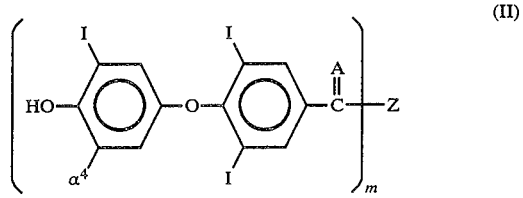

(II)

wherein:
m and Z have been defined previously;
$\alpha^4$ is hydrogen or iodine, and
A is oxygen or imine.

For the most part, the linking group to the G6PDH will be an amide (including the nitrogen analog thereof, i.e., amidine) or sulfonamide, usually an amide and will be derived from an available amino group of lysine, or a terminal amino group.

We have found that the PIA-G6PDH conjugates of the present invention provide distinct advantages over closely related polyiodothyronine G6PDH conjugates having longer linking groups when used in enzyme immunoassays. The conjugates of the present invention retain a substantial portion, about 50-60% of the original enzyme activity. The retained enzymatic activity can be inhibited by about 40-60% upon the binding to the conjugate of an antibody for a polyiodothyronine.

Polyiodothyronine analytes which can be detected in an assay employing the conjugates of the present invention for the most part have the following formula:

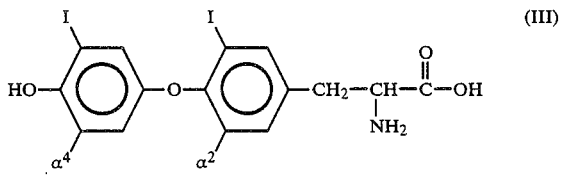

(III)

wherein $\alpha^2$ and $\alpha^4$ may both be iodine or one may be iodine and one hydrogen. Exemplary of such analytes are O-(4-hydroxy-3,5-diiodophenyl)-3,5-diiodotyrosine and O-(4-hydroxy-3-iodophenyl)-3,5-diiodotyrosine.

The PIA-G6PDH conjugates can be used in a wide variety of immunoassays, either employing a separation step (heterogeneous assays) or not employing a separation step (homogeneous assays). These types of assays have been extensively described in the literature, for example, see "Enzyme-Immunoassay," by Edward T. Maggio, CRC Press, Inc., Boca Raton, Fla., 1980; U.S. Pat. Nos. 3,817,837 and 3,935,074 (the disclosures of which are incorporated herein by reference); which listing is not intended to be exhaustive.

The assay can be run in at least two different ways. For illustrative purposes, thyroxine will be referred to.

In a heterogeneous manner, the PIA-G6PDH conjugate, sample, and antithyroxine antibody are combined in a suitable buffered medium, the mixture incubated for a sufficient time, and the enzyme conjugate bound to antibody separated from the unbound enzyme conjugate by any convenient means. For example, antibodies to anti-thyroxine are employed which aid in a clean separation of the enzyme conjugate-anti-thyroxine complex from the assay medium. The assay medium may then be examined for the enzyme activity of the remaining PIA-G6PDH conjugate.

In a homogeneous manner, the PIA-G6PDH conjugate, anti-thyroxine antibody and sample are combined and the combination is incubated for a sufficient time. The enzyme activity in the solution is determined without separation.

The amount of thyroxine in the sample is determined by comparing the results of the assay to known standards. For example, samples having known amounts of thyroxine are prepared and the assay carried out and the enzymatic activity determined. The enzymatic activity is then graphed against the thyroxine concentration and the graph used to determine the amount of thyroxine is an unknown.

The conditions for the assay will vary depending upon the particular method employed. Where the homogeneous technique is used, the conditions will be selected so as to optimize the change in activity of the enzyme conjugate upon binding by the receptor. Normally, the pH will be in the range of about 5.5 to 10, more usually in the range of about 7 to 9.5, where strong binding between receptor and thyroxine occurs. Moderate temperatures will be employed, normally in the range of about 0° to 45°, more usually about 20° to 40° C.

The buffer solution employed will normally be at a concentration to provide in the assay medium, a concentration of from about 0.001 to 0.5M, usually from about 0.01 to 0.2M. Protein will frequently be included to stabilize the enzyme; the protein can be an albumin, such as rabbit serum albumin, and/or gelatin, and will generally be present in about 0.005 to 0.5 weight percent in the final assay mixture, more usually from about 0.01 to 0.2 weight percent. Other additives may be present as found desirable, such as glycerol, Thimerosal, sodium azide, etc.

Concentration of the PIA-G6PDH conjugate will vary widely, depending on the concentration of polyiodothyronine of interest. Normally, the PIA-G6PDH conjugate concentration will be from about $10^{-5}$ to $10^{-13}$M, more usually from about $10^{-7}$ to $10^{-11}$M. The ratio of binding sites to the concentration of conjugated polyiodothyronine will generally be at least about 0.5 and not greater than 1000, more usually being about from 1 to 100.

The order of addition of the reagents is not critical. However, it is preferred that the PIA-G6PDH conjugate and receptor not be combined prior to the addition of the sample. The preferred order of addition is the sample and antibody, followed by the addition of enzyme conjugate. The particular substrates for the enzyme may be added as convenient. After each step the assay mixture may be incubated. Usually, incubation periods will be from about 10 seconds to 1 hour.

Enzyme activity determinations can be carried out for a duration of from about 5 seconds to 60 minutes, more usually being from about 0.25 to 30 minutes. For the most part, spectrophotometric techniques will be employed. However, other techniques include fluorimetry, titrimetry, etc.

The PIA-G6PDH conjugates can be prepared by techniques similar to those described in the literature. For example, conjugation of enzymes to low molecular weight compounds is described in U.S. Pat. No. 4,040,907, the disclosure of which is incorporated herein by reference. For example, a non-oxo-carbonyl group, e.g., carboxyl group, on the PIA can be activated for reaction with amine groups on the G6PDH by formation of an ester with N-hydroxysuccinimide.

The following examples are offered by way of illustration and not by way of limitation.

EXPERIMENTAL (All temperatures not otherwise indicated are in Centigrade. All percents not otherwise indicated are by weight.)

EXAMPLE 1

Conjugation of G6PDH to 4-(4-hydroxy-3,5-diiodophenoxy)-3,5-diiodobenzoic acid (HDDA)

The N-hydroxysuccinimide (NHS) ester of HDDA was prepared by a conventional method (see U.S. Pat. No. 4,040,907). Dicyclohexylcarbodiimide (32 mg) (DCC), HDDA (100 mg), and NHS (17.4 mg) were combined in one ml tetrahydrofuran (THF) as a solvent. The ester formed readily at room temperature as indicated by the formation of a white insoluble precipitate—dicyclohexylurea (DCU). The reaction was allowed to continue overnight at room temperature.

The DCU precipitate was removed by filtration and the clear filtered ester solution had a slight yellow color. The THF was removed by rotary evaporation. The dry ester was dissolved in dry DMF, refiltered and was then ready for conjugation to G6PDH. Native G6PDH was dialyzed overnight at 4° C. with 3 changes of 0.05M phosphate buffer pH 8.5 (no preservatives). The concentration of enzyme used was 4 to 6 mg/ml. DMF was then added to the enzyme solution slowly to a 20% (v/v) ratio. The pH was maintained at 9 during conjugation.

Small aliquots of the enzyme were taken after each hapten addition to follow % deactivation and % inhibition. Deactivation should not be allowed to exceed 60%.

The HDDA-G6PDH conjugate was chromatographed on Sephadex G-100 column equilibrated with basic buffer (55 mM Tris with NaN$_3$ and Thimerosal) including 1% Tween-20. Fractions with activity were pooled and any precipitate was removed by filtration using a 0.45μ Millipore filter. The HDDA-G6PDH conjugate exhibited an enzyme activity of 50% of that of the unconjugated enzyme. On the average each molecule of G6PDH contained 6-10 HDDA units.

EXAMPLE 2

Assay

Assay Protocol

The formulations for reagents employed are listed below:

Pretreated sample—serum sample pretreated in accordance with the procedure described in U.S. Pat. No. 4,121,975 (the relevant disclosure thereof being incorporated herein by reference).
0.25M, NaOH
0.25%, α-cyclodextrin
0.025%, Salicylic Acid

| | Assay Buffer |
|---|---|
| 200 mM | Tris Base |
| 0.01% | NaN$_3$ |
| 0.001% | Thimerosal |
| | pH 8.5 |
| | Antibody Diluent (Reagent A) |
| 300 mM | Glucose-6-phosphate.1, sodium |
| 300 mM | NAD$^+$ |
| 1.0% | BSA |
| 200 mM | Tris Base |
| 0.05% | NaN$_3$ |
| 0.005% | Thimerosal |
| | pH 5.5 |
| | Enzyme Diluent (Reagent B) |
| 1% | BSA |
| 0.9% | NaCl |
| 55 mM | Tris Base |
| 0.05% | NaN$_3$ |
| 0.005% | Thimerosal |
| | pH 8.0 |

Calibrators were prepared by dissolving known amounts of thyroxine in thyroxine free human serum at levels of 20, 40, 80, 120, and 200 ng/ml The stepwise testing protocol for the assay was as follows:

1. 40 μl calibrator + 100 μl pretreated sample into beaker #1.
2. 50 μl Reagent A + 300 μl Assay Buffer into beaker #1.
3. 50 μl Reagent B + 300 μl Assay Buffer into beaker #1.
4. Aspirate into a flow cell for the Stasar III spectrophotometer
   37° C.
   340 nm
   10 sec delay
   30 sec read time The results were as follows:
mean = 6.75 μg/dl
S.D. = 0.27 μg/dl
CV% = 4.07%
N = 16

The results of the foregoing example demonstrate that extremely low concentrations, as well as extremely small amounts of thyroxine can be detected by a method employing the PIA-G6PDH conjugates of the present invention. The method is quite straightforward in requiring few manipulative steps. By combining the reagents in a buffered medium, and optionally incubating the mixture, followed by the addition of the enzyme substrates, one can determine a polyiodothyronine analyte by a spectrophotometric reading over a short period of time. The system allows for automation, so that samples and reagents can be mixed automatically and read. The PIA-G6PDH conjugates offer a distinct advantage over closely related compounds having a linking group between the enzyme and the polyiodothyronine longer than a chain one atom in length. Compounds possessing such longer linking group, when used in the above assay, did not give meaningful results.

Although the foregoing invention has been described in some detail by way of illustration and example for purposes of clarity of understanding, it will be obvious that certain changes and modifications may be practiced within the scope of the appended claims.

What is claimed is:

1. A compound of the formula:

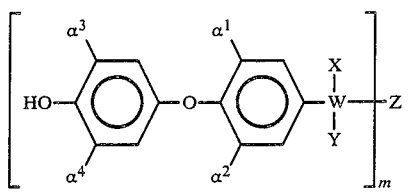

(I)

wherein:
Z is glucose-6-phosphate dehydrogenase;
$\alpha^1$ to $\alpha^4$ are selected from the group consisting of iodine, bromine, tert-butyl and hydrogen; wherein no more than one $\alpha$ is hydrogen;
W is carbon or sulfur;
X is oxygen when W is sulfur; or when W is carbon X may be taken together with Y to form a double bond to carbon wherein the carbon contains two substituents each substituent having 1 to 5 atoms selected from the group consisting of carbon, hydrogen, oxygen, nitrogen, and sulfur, to oxygen, to imine nitrogen or to sulfur or X is otherwise hydrogen;
Y is oxygen when W is sulfur, or Y is a substituent having 1-5 atoms selected from a group consisting of carbon, hydrogen, oxygen, nitrogen and sulfur; and
m is a number from 1 to 16.

2. The compound of claim 1 wherein W is carbon.

3. The compound of claim 1 wherein W is carbon and X is taken together with Y to form oxo.

4. The compound of claim 1 wherein $\alpha^1-\alpha^4$ are selected from a group consisting of iodine and hydrogen.

5. The compound of claim 1 wherein $\alpha^1$ to $\alpha^4$ are iodine.

6. A compound of the formula:

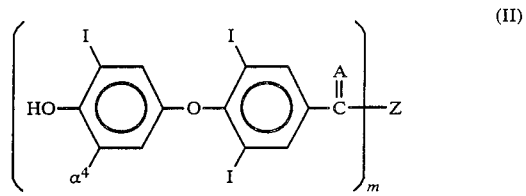

(II)

wherein:
$\alpha^4$ is iodine or hydrogen;
Z is glucose-6-phosphate dehydrogenase;
m is a number from 3 to 8; and
A is oxygen or imine (NH).

7. The compound of claim 6 wherein $\alpha^4$ is iodine and A is oxygen.

8. A method for detecting the presence or amount of a polyiodothyronine in a sample suspected of containing the same, which method comprises:
combining in an aqueous medium the sample, the compound of claim 1, and an antibody specific for the polyiodothyronine, and
determining the enzyme activity of said medium wherein the enzyme activity is related to the amount of polyiodothyronine in the sample.

9. A method for detecting the presence or amount of a polyiodothyronine in a sample suspected of containing the same, which method comprises:
combining in an aqueous medium the sample, the compound of claim 6, and an antibody specific for the polyiodothyronine, and
determining the enzyme activity of said medium wherein the enzyme activity is related to the amount of polyiodothyronine in the sample.

10. In an homogeneous enzyme immunoassay method for detecting the presence or amount of a polyiodothyronine in a sample suspected of containing the same, said method employing a conjugate of an enzyme and a polyiodothyronine, the improvement which comprises employing the compound of claim 1 as the conjugate.

11. In an homogeneous enzyme immunoassay method for detecting the presence or amount of a polyiodothyronine in a sample suspected of containing the same, said method employing a conjugate of an enzyme and a polyiodothyronine, the improvement which comprises employing the compound of claim 6 as the conjugate.

* * * * *